(12) United States Patent
Tamez-Peña et al.

(10) Patent No.: US 6,836,557 B2
(45) Date of Patent: Dec. 28, 2004

(54) METHOD AND SYSTEM FOR ASSESSMENT OF BIOMARKERS BY MEASUREMENT OF RESPONSE TO STIMULUS

(75) Inventors: José Tamez-Peña, Rochester, NY (US); Saara Marjatta Sofia Totterman, Rochester, NY (US); Edward Ashton, Webster, NY (US)

(73) Assignee: VirtualScopics, LLC, Rochester, NY (US)

(*) Notice: Subject to any disclaimer, the term of this patent is extended or adjusted under 35 U.S.C. 154(b) by 0 days.

(21) Appl. No.: 10/262,671

(22) Filed: Oct. 2, 2002

(65) Prior Publication Data

US 2004/0066955 A1 Apr. 8, 2004

(51) Int. Cl.⁷ .................................................. G06K 9/00
(52) U.S. Cl. ..................................................... 382/128
(58) Field of Search ................................ 382/128, 131, 382/132; 324/300, 307, 309; 600/410, 425, 443; 708/4, 62, 21

(56) References Cited

U.S. PATENT DOCUMENTS

| | | | | |
|---|---|---|---|---|
| 5,170,347 A | * | 12/1992 | Tuy et al. | 345/419 |
| 5,257,625 A | * | 11/1993 | Pelc | 600/410 |
| 5,476,096 A | * | 12/1995 | Olstad et al. | 600/443 |
| 5,818,231 A | * | 10/1998 | Smith | 324/309 |
| 6,112,112 A | * | 8/2000 | Gilhuijs et al. | 600/425 |
| 6,169,817 B1 | * | 1/2001 | Parker et al. | 382/131 |
| 6,204,853 B1 | * | 3/2001 | Cline et al. | 345/424 |
| 6,411,729 B1 | * | 6/2002 | Grunkin | 382/132 |
| 6,556,696 B1 | * | 4/2003 | Summers et al. | 382/128 |
| 6,608,628 B1 | * | 8/2003 | Ross et al. | 345/619 |
| 6,625,303 B1 | * | 9/2003 | Young et al. | 382/132 |
| 6,633,686 B1 | * | 10/2003 | Bakircioglu et al. | 382/294 |

* cited by examiner

Primary Examiner—Jose L. Couso
(74) Attorney, Agent, or Firm—Blank Rome LLP (57) ABSTRACT

In a human or animal organ or other region of interest, specific objects, such as liver metastases and brain lesions, serve as indicators, or biomarkers, of disease. In a three-dimensional image of the organ, the biomarkers are identified and quantified both before and after a stimulus is applied, and their reaction to the stimulus is observed. Statistical segmentation techniques are used to identify the biomarker in a first image and to carry the identification over to the remaining images.

34 Claims, 2 Drawing Sheets

METHOD AND SYSTEM FOR ASSESSMENT OF BIOMARKERS BY MEASUREMENT OF RESPONSE TO STIMULUS

FIELD OF THE INVENTION

The present invention is directed to the assessment of certain biologically or medically significant characteristics of bodily structures, known as biomarkers, and more particularly to the assessment of biomarkers by quantitative measurement of their response to a stimulus.

DESCRIPTION OF RELATED ART

The measurement of internal organs and structures from computed tomography (CT), magnetic resonance imaging (MRI), ultrasound, positron emission tomography (PET), and other imaging data sets is an important objective in many fields of medicine. These imaging modalities are quantitative assessments that, when used, are typically based on manual intervention by a trained technician or radiologist. Examples illustrating current applications of medical imaging include the measurement of the hippocampus in patients with epilepsy (Ashton E. A., Parker K. J., Berg M. J., and Chen C. W. "A Novel Volumetric Feature Extraction Technique with Applications to MR Images," *IEEE Transactions on Medical Imaging* 16:4, 1997), the measurement of the biparietal diameter of the fetal head, and the measurement of cartilage thickness in bone (Stammberger, T., Eckstein, F., Englmeier, K-H., Reiser, M. "Determination of 3D Cartilage Thickness Data from MR Imaging: Computational Method and Reproducibility in the Living," *Magnetic Resonance in Medicine* 41, 1999; and Stammberger, T., Hohe, J., Englmeier, K-H., Reiser, M., Eckstein, F. "Elastic Registration of 3D Cartilage Surfaces from MR Image Data for Detecting Local Changes in Cartilage Thickness", *Magnetic Resonance in Medicine* 44, 2000).

The need for accurate and precise measurements of organs, tissues, structures, and sub-structures continues to increase. For example, in following the response of a disease to a new therapy, the accurate representation of three-dimensional (3D) structures is vital in broad areas such as neurology, oncology, orthopedics, and urology. In human and animal anatomy texts, there are a great number of named organs, structures, and sub-structures. Furthermore, in disease states modifications to normal structures are possible and additional pathological structures or lesions can be present. Despite the imposing number of defined substructures and pathologies, within the major disease categories there are specific objects that serve as indicators of disease. For example, liver metastases, brain lesions, atherosclerotic plaques, and meniscal tears are some examples of specific indicators of different conditions. The topological, morphological, radiological, and pharmacokinetic characteristics of biological structures and sub-structures are called biomarkers, and specific measurements of the biomarkers can provide a quantitative assessment of disease progress. The ability to clearly and precisely quantify, distinguish and identify these biomarkers represents a needed and important step for an accurate, image-based assessment of both normal and disease states. Currently, medical imaging techniques such as MRI, CT, and ultrasound are used to assess biological structures and substructures and offer a limited degree of resolution.

In following the response of a person or animal to therapy, or to monitor the progression of disease, it is desirable to accurately and precisely monitor the trends in biomarkers over time. It is also very useful to obtain accurate measurements of these biomarkers over time, particularly to judge the degree of response to a new therapy, or to assess the trends often associated with increasing age. The prior art is capable of assessing gross changes over time. However, the conventional measurements are not well suited to assessing and quantifying subtle changes in lesion size, and are incapable of describing complex topology or shape in an accurate manner or of addressing finer details of biological structure(s).

In consideration of current medical imaging and tracking techniques, it becomes apparent that there are many disadvantages in using such technologies. As was noted earlier, many current imaging modalities require manual or semi-manual intervention by trained personnel. Interventions often include the usage of calipers (to derive measurement from radiographic films) and/or the use of a trackball or mouse. Additionally, user assisted interfaces are also employed to initiate some semi-automated algorithms (Ashton et al). The need for intensive and expert manual intervention is a disadvantage, since the demarcations can be tedious and prone to a high inter- and intra-observer variability. Furthermore, the typical application of manual measurements within two-dimensional (2D) slices, or even sequential 2D slices within a 3D data set, is not optimal since tortuous structures, curved structures, and thin structures are not well characterized within a single 2D slice, leading again to operator confusion and high variability in results. If these measurements are repeated over time on successive scans, then inaccurate trend information can unfortunately be obtained.

Yet another problem with conventional methods is that they lack sophistication and are based on "first order" measurements of diameter, length, or thickness. These traditional measurements can be insensitive to small but important changes. As previously mentioned, the manual and semi-manual tracings of images lead to high intra- and inter-observer variability, and also lead to uneven or "ragged" 3D structures. The accuracy of these measurements and their sensitivity to subtle changes in small sub-structures are highly dependent upon the resolution of the imaging system. Unfortunately, most CT, MRI, and ultrasound systems have poor resolution in the out-of-plane, or "z" axis. While the in-plane resolution of these systems can commonly resolve objects that are just less than one millimeter in separation, the out-of-plane (slice thickness) is commonly set at 1.5 mm or even greater. For assessing subtle changes and small defects using "higher order" structural measurements, it is desirable to have better than one millimeter resolution in all three orthogonal axes. Manual and semi-manual assessments of conventional biomarkers (such as major axis length or cross-sectional area) have a high inherent variability, so as successive scans are traced the variability can hide subtle trends. This means that only gross changes, sometimes over very long time periods, can be verified using conventional methods.

Some references for the prior work include:

Eckstein F., Gavazzeni H. S., Sittek H., Haubner, M., Losch, A., Milz, S., Englmeier, K-H., Schulte, E., Putz, R, Reiser, M. "Determination of Knee Joint Cartilage Thickness using Three-Dimensional Magnetic Resonance Chondro-Crassometry (3D MR-CCM)," *Magnetic Resonance in Medicine* 36: 256–265, 1996.

Solloway, S., Hutchinson, C. E., Waterton, J. C., Taylor, C. "The Use of Active Shape Models for Making Thickness Measurements of Articular Cartilage from MR Images," *Magnetic Resonance in Medicine* 37: 943–952, 1997.

Stammberger, T., Eckstein, F., Englmeier, K-H., Reiser, M. "Determination of 3D Cartilage Thickness Data from MR Imaging: Computational Method and Reproducibility in the Living," *Magnetic Resonance in Medicine* 41: 529–536, 1999.

Ghosh, S., Ries, M., Lane, N., Majundar, S. "Segmentation of High Resolution Articular Cartilage MR Images," 46th Annual Meeting, Orthopaedic Research Society, Mar. 12–15, 2000, Orlando Fla.

Dardzinski, B. J., Mosher, T. J., Li, S., Van Slyke, M. A., Smith, M. B. "Spatial Variation of T2 in Human Articular Cartilage. *Radiology* 205: 546–550, 1997.

Therasse, P., et al. "New Guidelines to Evaluate the Response to Treatment in Solid Tumors," *Journal of National Cancer Institute*, February 2000(92) 3: 205–216. This paper describes the standard (RECIST) for unidimensional tumor measurement.

Barseghian, T. "Uterine Fibroid Embolization Offers Alternative to Surgery," *Diagnostic Imaging*, September 1997, 11–12. This paper illustrates the awkwardness of the conventional mouse-driven manual outlining of lesions.

Yang, W., et al., "Comparison of Dynamic Helical CT and Dynamic MR Imaging in the Evaluation of Pelvic Lymph Nodes in Cervical Carcinoma," *American Journal of Roentgenology,* 2000 September; 175(3): 759–766.

Hermans, R., et al. "The Relation of CT-Determined Tumor Parameters and Local and Regional Outcome of Tonsillar Cancer after Definitive Radiation Treatment," *International Journal of Radiation Oncology Biology-Physics.* 2001 May 1; 50(1): 37–45.

Rovaris M, Inglese M, van Shijndel R A, et al. "Sensitivity and reproducibility of volume change measurements of different brain portions on magnetic resonance imaging in patients with multiple sclerosis," *Journal of Neurology.* 247(12): 960–965, 2000.

Sahani, D., et al. "Quantitative Measurements of Medical Images for Pharmaceutical Clinical Trials: Comparison Between On and Off-Site Assessments," *American Journal of Roentgenology*, 2000 April; 174(4): 1159–1162.

The following references disclose prior art which is relevant but has limitations that the present invention transcends:

Prior work by Gilhuijs et al, U.S. Pat. No. 6,112,112, uses variance processing to derive a variance image. However, this work concerns changes in intensity as contrast agents flow into and out of a tumor.

Other work by Brasch et al, U.S. Pat. No. 6,009,342, attempts to determine a kinetic model of microvascular permeability. However, this work also pertains to the uptake and wash-out of contrast agents.

Other work by Scarth et al, U.S. Pat. No. 6,064,770, seeks to detect novelties in a data set, using the fuzzy C-Means clustering algorithm.

Other work by Olstad et al, U.S. Pat. No. 5,476,096, considers the processing of real-time ultrasound data sets in a way that is reminiscent of digital subtraction angiography.

SUMMARY OF THE INVENTION

In light of the aforementioned disadvantages, it becomes apparent that there is a clear need for improved imaging systems and methods. Moreover, there is a need for an invention which utilizes "higher order" measurements to provide a previously unknown degree of resolution and quantification of biomarkers from their respective medical imaging data sets. Additionally, there is a need for an invention that incorporates these highly accurate and definitive images into a contiguous temporal framework, thus providing an accurate definition of trends over time.

Clearly, a need exists for improvement upon: (1) earlier methods of assessing and quantifying structures; (2) assessing the response of biomarkers in response to stimuli; (3) tracking change(s) of biological structure(s) and/or sub-structures over time; and (4) incorporating "higher order" measurements. More precisely, there is a clear need for measurements that are more accurate and precise, with lower variability than conventional manual or semi-manual methods. There is furthermore a need for more accurate and precise assessment and measurement of biomarkers in response to stimuli. There is furthermore a need for measurements that are accurate over time, as repeated measurements are made. There is furthermore a need for measurements based on high-resolution data sets, such that small defects, tortuous objects, thin objects, and curved objects, can be quantified. Finally there is a need for measurements, parameters, and descriptors which are more sophisticated, more representative and more sensitive to subtle changes than the simple "first order" measurements of length, diameter, thickness, area and volume.

To achieve the above and other objects, the present invention is directed to a system and method for accurately and precisely identifying important structures and sub-structures, their normalities and abnormalities, and their specific topological and morphological characteristics—all of which are sensitive indicators of disease processes and related pathology. Biomarker measurements both before and after a stimulus are taken, so that the response of the biomarker to the stimulus can be determined. A stimulus can be applied (e.g., force, energy, or a chemical substance) or can be naturally occurring (e.g., disease progression).

The preferred technique is to identify the biomarkers based on automatic techniques that employ statistical reasoning to segment the biomarker of interest from the surrounding tissues (the statistical reasoning is given in Parker et al., U.S. Pat. No. 6,169,817, whose disclosure is hereby incorporated by reference in its entirety into the present disclosure). This can be accomplished by fusion of a high resolution scan in the orthogonal, or out-of-plane direction, to create a high resolution voxel data set (Peña, J.-T., Totterman, S. M. S., Parker, K. J. "MRI Isotropic Resolution Reconstruction from Two Orthogonal Scans," *SPIE Medical Imaging,* 2001). In addition to the assessment of subtle defects in structures, this high-resolution voxel data set enables more accurate measurement of structures that are thin, curved, or tortuous. More specifically, this invention improves the situation in such medical fields as oncology, neurology, and orthopedics. In the field of oncology, for example, the invention is capable of identifying tumor margins, specific sub-components such as necrotic core, viable perimeter, and development of tumor vasculature (angiogenesis), which are sensitive indicators of disease progress or response to therapy. Similarly, in the fields of neurology and orthopedics, the invention is capable of identifying characteristics of both the whole brain and prosthesis wear, respectively.

Generally speaking, biomarkers are biological structures and are thus subject to change in response to a variety of things. For example, the brain volume in a patient with multiple sclerosis may diminish after a period of time. In this case, a disease (multiple sclerosis) has caused a change in a biomarker (brain volume). More information on biomarkers and their use is found in the applicants' co-pending U.S.

patent application Ser. No. 10/189,476, filed Jul. 8, 2002, whose disclosure is hereby incorporated by reference in its entirety into the present disclosure. For a physician attempting to effectively monitor the progress of a disease via an image-based platform, an accurate, precise and temporally contiguous picture of the progress of the disease is needed. In light of the current state of imaging technology, however, the ability to accurately and precisely monitor disease progress on an image-based platform is non-existent. Thus, there is a need for the accurate and precise assessment of biomarkers by measuring their response to a stimulus. Per the present invention, the inventors define a stimulus as some applied force, substance, or energy that produces an effect or alteration in a biomarker. Stimuli include, but are not limited to:

- any type of energy [e.g., ionizing energy, heat energy (temperature), non-ionizing energy]
- any type of externally applied force (e.g., loading, mechanical stress/movement, motion)
- any type of treatment modality (e.g., chemotherapy, radiation therapy, therapeutic compounds)
- any type of disease process, including congenital, developmental, and infectious processes.

More specific examples of biomarkers that respond to stimuli include multiple sclerosis (lesion volume, whole brain volume, volume of a particular part of the brain, and intra-cranial cerebrospinal fluid volume), cancer (lesion volume, lesion surface area within one CT or MRI slice, major and minor axes within one slice, and the cross product of major and minor axes within one slice), and osteoarthritis (cartilage thickness, cartilage volume, image intensity of the cartilage and bone, and T2 relaxation time of the cartilage). This invention provides an improved system and method for assessing biomarkers in response to stimuli. This improvement is brought about by other improvements in the areas pertaining to the assessment and quantification of biomarkers, tracking changes of structures over time, and the sophistication of imaging methods.

It is desirable to accurately and precisely monitor the trends in biomarkers over time by assessing the response to a stimulus. For example, it is useful to monitor the condition of trabecular bone in patients with osteoarthritis. The inventors have discovered that extracting a biomarker using statistical tests and treating the biomarker over time as a four-dimensional (4D) object, with an automatic passing of boundaries from one time interval to the next, can provide a highly accurate and reproducible segmentation from which trends over time can be detected. This preferred approach is defined in the above-cited U.S. Pat. No. 6,169,817. Thus, this invention improves the situation by combining selected biomarkers that themselves capture subtle pathologies, with a 4D approach to increase accuracy and reliability over time, to create a sensitivity that has not been previously obtainable.

Although the conventional measures of length, diameter, and their extensions to area and volume are quite useful quantities, they are limited in their ability to assess subtle but potentially important features of tissue structures or substructures. Thus, the inventors propose to use "higher order" measures of structure and shape to characterize biomarkers. The inventors define "higher order" measures as any measurements that cannot be extracted directly from the data using traditional manual or semi-automated techniques, and that go beyond simple pixel counting. Length, area, and volume measurements are examples of simple first-order measurements that can be obtained by pixel counting. These higher order measures include, but are not limited to:

- eigenfunction decompositions
- moments of inertia
- shape analysis, including local curvature
- results of morphological operations such as skeletonization
- fractal analysis
- 3D wavelet analysis
- advanced surface and shape analysis such as a 3D spherical harmonic analysis with scale invariant properties
- trajectories of bones, joints, tendons, and moving musculoskeletal structures Mathematical theories of these higher order measurements can be found in Kaye, B. H., "Image Analysis Procedures for Characterizing the Fractal Dimension of Fine Particles," Proc. Part. Tech. Conference, 1986; Ashton, E. et al., "Spatial-Spectral Anomaly Detection with Shape-Based Classification," Proc. Military Sensing Symposium on Targets, Backgrounds and Discrimination, 2000; and Struik, D. J., *Lectures on Classical Differential Geometry*, 2nd ed., New York: Dover, 1988.

The present invention represents a resolution to the needs noted above. Moreover, and in sum, the present invention provides a method and system for the precise and sophisticated measurement of biomarkers, the accurate definition of trends over time, and the assessment of biomarkers by measurement of their response to a stimulus.

The measurement of internal organs and structures via medical imaging modalities (i.e., MRI, CT and ultrasound) provides invaluable image data sets for use in a variety of medical fields. These data sets permit medical personnel to objectively measure an object or objects of interest. Such objects may be deemed biomarkers and, per this invention, the inventors choose to define biomarkers as the abnormality and normality of structures, along with their topological and morphological characteristics and parameters, which may serve as sensitive indicators of disease, disease progress, and any other associated pathological state. For example, a physician examining a cancer patient may employ either MRI or CT scan technology to measure any number of pertinent biomarkers, such as tumor compactness, tumor volume, and/or tumor surface roughness.

The inventors have discovered that the following new biomarkers are sensitive indicators of the progress of diseases characterized by solid tumors in humans and in animals.

The following biomarkers relate to cancer studies:

Tumor surface area

Tumor compactness (surface-to-volume ratio)

Tumor surface curvature

Tumor surface roughness

Necrotic core volume necrotic core compactness necrotic core shape

Viable periphery volume

Volume of tumor vasculature

Change in tumor vasculature over time

Tumor shape, as defined through spherical harmonic analysis

Morphological surface characteristics lesion characteristics tumor characteristics tumor peripheral characteristics tumor core characteristics bone metastases characteristics
ascites characteristics
pleural fluid characteristics
vessel structure characteristics
neovasculature characteristics
polyp characteristics
nodule characteristics
angiogenisis characteristics
tumor length
tumor width
tumor 3D volume.

The inventors have also discovered that the following new biomarkers are sensitive indicators of osteoarthritis joint disease in humans and in animals:

shape of the subchondral bone plate
layers of the cartilage and their relative size
signal intensity distribution within the cartilage layers
contact area between the articulating cartilage surfaces
surface topology of the cartilage shape
intensity of bone marrow edema
separation distances between bones
meniscus shape
meniscus surface area
meniscus contact area with cartilage
cartilage structural characteristics
cartilage surface characteristics
meniscus structural characteristics
meniscus surface characteristics
pannus structural characteristics
joint fluid characteristics
osteophyte characteristics
bone characteristics
lytic lesion characteristics
prosthesis contact characteristics
prosthesis wear
joint spacing characteristics
tibia medial cartilage volume
Tibia lateral cartilage volume
femur cartilage volume
patella cartilage volume
tibia medial cartilage curvature
tibia lateral cartilage curvature
femur cartilage curvature
patella cartilage curvature
cartilage bending energy
subchondral bone plate curvature
subchondral bone plate bending energy
meniscus volume
osteophyte volume
cartilage T2 lesion volumes
bone marrow edema volume and number
synovial fluid volume
synovial thickening
subchondrial bone cyst volume and number
kinematic tibial translation
kinematic tibial rotation
kinematic tibial valcus
distance between vertebral bodies
degree of subsidence of cage
degree of lordosis by angle measurement
degree of off-set between vertebral bodies
femoral bone characteristics
patella characteristics.

The inventors have also discovered that the following new biomarkers are sensitive indicators of neurological disease in humans and in animals:

The shape, topology, and morphology of brain lesions
The shape, topology, and morphology of brain plaques
The shape, topology, and morphology of brain ischemia
The shape, topology, and morphology of brain tumors
The spatial frequency distribution of the sulci and gyri
The compactness (a measure of surface to volume ratio) of gray matter and white matter
whole brain characteristics
gray matter characteristics
white matter characteristics
cerebral spinal fluid characteristics
hippocampus characteristics
brain sub-structure characteristics
The ratio of cerebral spinal fluid volume to gray mater and white matter volume
The number and volume of brain lesions.

The following biomarkers are sensitive indicators of disease and toxicity in organs:

organ volume
organ surface
organ compactness
organ shape
organ surface roughness
fat volume and shape.

BRIEF DESCRIPTION OF THE DRAWING

A preferred embodiment of the present invention will be set forth in detail with reference to the drawings, in which.

DETAILED DESCRIPTION OF THE PREFERRED EMBODIMENT

A preferred embodiment of the present invention will now be set forth in detail with reference to the drawings.

Figure 1:
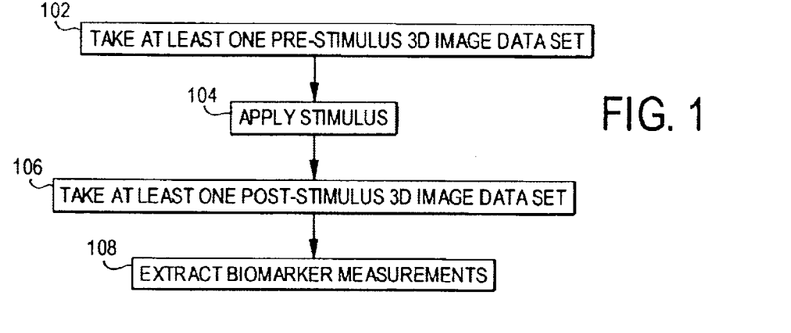
FIG. 1 shows a flow chart of operational steps performed in the preferred embodiment.

An overview of the operational steps carried out in the preferred embodiment is shown in FIG. 1. In step 102, one or more 3D image data sets are taken in a region of interest in the patient before the application of a stimulus. The 3D image data sets can be taken by any suitable technique, such as MRI; if there are more than one, they are separated by time to form a time sequence of images. In step 104, a stimulus is applied to a portion within the region of interest constituting the biomarker. For example, if the biomarker is the 3D volume of a tumor, the stimulus can be the application of radiotherapy to the tumor. Of course, in the case of a naturally occurring stimulus such as disease progression, no affirmative action by the operator is required. In step 106, one or more 3D image data sets are taken again, as in step 102, except after the stimulus. In step 108, the biomarker measurements are extracted from the image data sets taken before and after the stimulus. With those measurements, the reaction of the biomarker to the stimulus can be determined.

The extraction of the biomarker information in step 108 will now be explained. Conventionally, structures of interest have been identified by experts, such as radiologists, with manual tracing. As previously mentioned, the manual and semi-manual tracings of images lead to high intra- and inter-observer variability, and also lead to uneven or "ragged" 3D structures. The preferred method is to identify the biomarkers based on automatic techniques that employ statistical reasoning to segment the biomarker of interest from the surrounding tissues. The statistical reasoning is defined in the above-cited U.S. Pat. No. 6,169,817. From raw image data obtained through magnetic resonance imaging or the like, an object is reconstructed and visualized in four dimensions (both space and time) by first dividing the first image in the sequence of images into regions through statistical estimation of the mean value and variance of the image data and joining of picture elements (voxels) that are sufficiently similar and then extrapolating the regions to the remainder of the images by using known motion characteristics of components of the image (e.g., spring constants of muscles and tendons) to estimate the rigid and deformational motion of each region from image to image. The object and its regions can be rendered and interacted with in a four-dimensional (4D) virtual reality environment, the four dimensions being three spatial dimensions and time.

Figure 2:
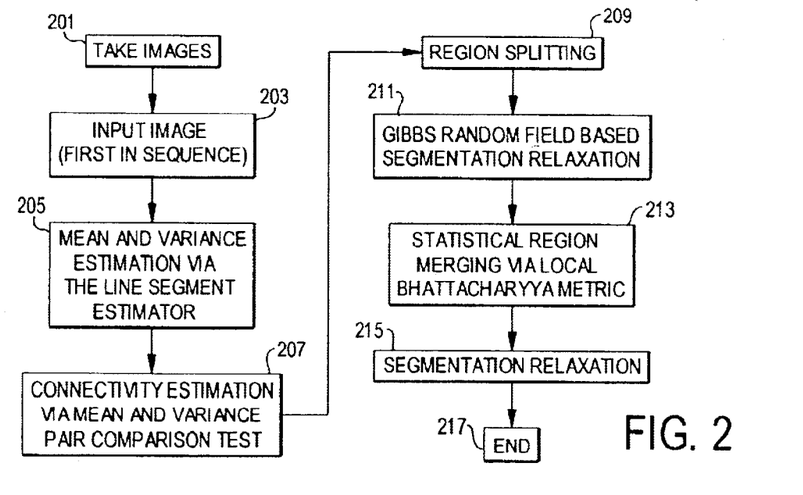
FIG. 2 shows a flow chart of a segmentation process used in the process of FIG. 1.

The segmentation will be explained with reference to FIG. 2. First, at step 201, the images in the sequence are taken, as by an MRI. Raw image data are thus obtained. Then, at step 203, the raw data of the first image in the sequence are input into a computing device. Next, for each voxel, the local mean value and region variance of the image data are estimated at step 205. The connectivity among the voxels is estimated at step 207 by a comparison of the mean values and variances estimated at step 205 to form regions. Once the connectivity is estimated, it is determined which regions need to be split, and those regions are split, at step 209. The accuracy of those regions can be improved still more through the segmentation relaxation of step 211. Then, it is determined which regions need to be merged, and those regions are merged, at step 213. Again, segmentation relaxation is performed, at step 215. Thus, the raw image data are converted into a segmented image, which is the end result at step 217. Further details of any of those processes can be found in the above-cited patent.

Prior methods for measuring temporal changes in biological structures and/or sub-structures were generally performed by manual measurements on sequential 2D slice data within a 3D data set. As was previously mentioned, this method is not optimal since tortuous structures (e.g., vasculature), curved structures (e.g., brain contour), and thin structures (e.g., cartilage) are not well characterized within a single 2D slice, leading again to operator confusion and high variability in results. This invention improves the situation by identifying important structures or substructures, their normalities and abnormalities, and their specific topological and morphological characteristics, which are sensitive indicators of disease and the pathological state. This improved identification, coupled with our method of extracting the biomarker by statistical means and treating it (the biomarker) as a 4D object over time, creates a sensitivity to tracking changes over time of biomarkers that has not been previously attainable.

In following the response of a person or animal to therapy, or to monitor the progression of disease, it is desirable to accurately and precisely monitor the trends in biomarkers over time. This is difficult to do in conventional practice since repeated scans must be reviewed independently and the biomarkers of interest must be traced or measured manually or semi-manually with each time interval representing a new and tedious process for repeating the measurements. It is highly advantageous to take a 4D approach, such as was defined in U.S. Pat. No. 6,169,817, where a biomarker is identified with statistical reasoning, and the biomarker is tracked from scan to scan over time. That is, the initial segmentation of the biomarker of interest is automatically passed on to the data sets from scans taken at later intervals. A search is done to track the biomarker boundaries from one scan to the next. Note that the sense of time in a series of scans can be reversed for convenience in performing an analysis. That is, the biomarker in the last scan can be segmented initially, then the results can be back propagated through the previous scans. Or, in a long sequence of scans over time, a mid-point scan can be analyzed first, and the results of the biomarker identification propagated both forward and backwards from that point. The mid-point scan may or may coincide in time with the application of the stimulus. The accuracy, precision and reproducibility of this approach is superior to that of performing manual or semi-manual measurements on images with no automatic tracking or passing of boundary information from one scan interval to subsequent scans.

Figure 3:
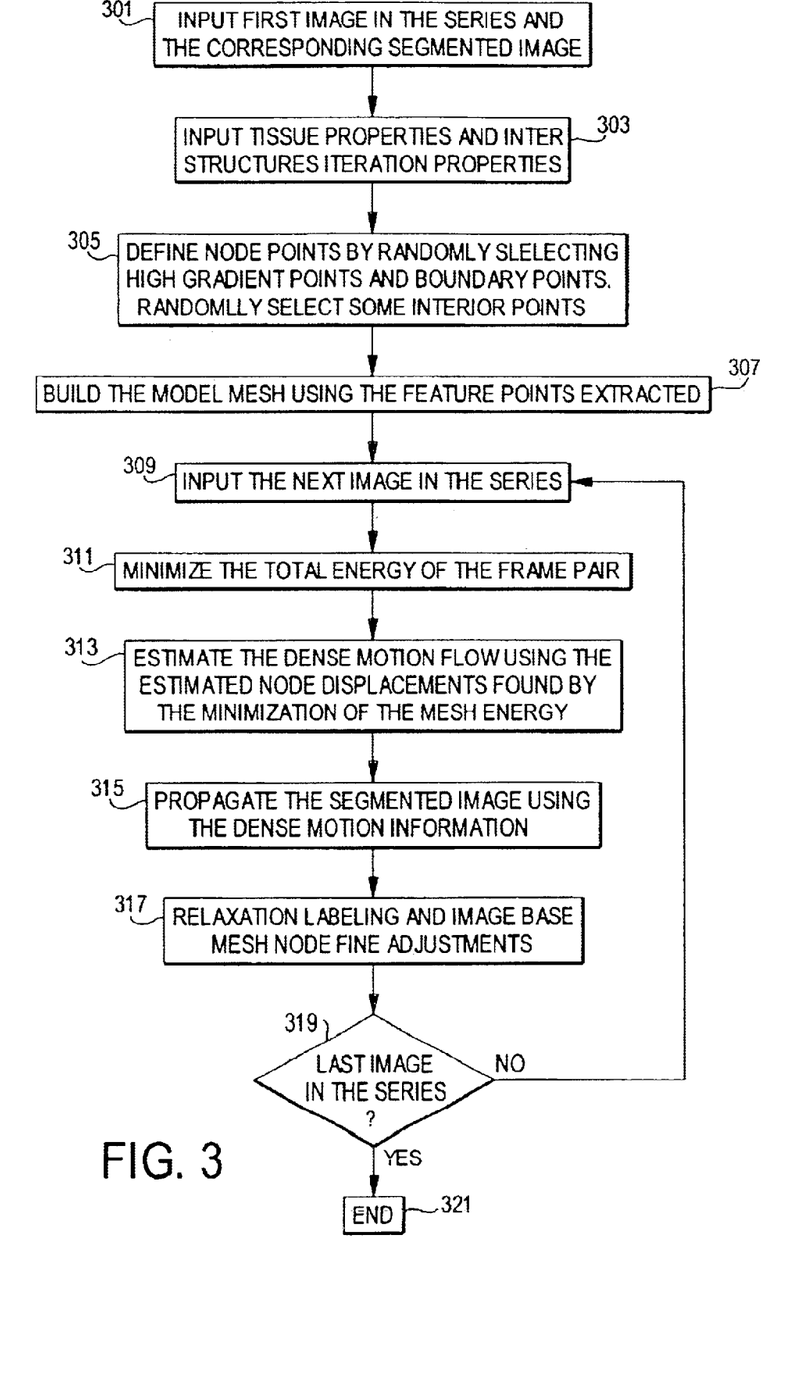
FIG. 3 shows a process of tracking a segmented image in multiple images taken over time.

The creation of a 4D model (in three dimensions of space and one of time) will be described with reference to FIG. 3. A motion tracking and estimation algorithm provides the information needed to pass the segmented image from one frame to another once the first image in the sequence and the completely segmented image derived therefrom as described above have been input at step 301. The presence of both the rigid and non-rigid components should ideally be taken into account in the estimation of the 3D motion. According to the present invention, the motion vector of each voxel is estimated after the registration of selected feature points in the image.

To take into consideration the movement of the many structures present in a joint, the approach of the present invention takes into account the local deformations of soft tissues by using a priori knowledge of the material properties of the different structures found in the image segmentation. Such knowledge is input in an appropriate database form at step 303. Also, different strategies can be applied to the motion of the rigid structures and to that of the soft tissues. Once the selected points have been registered, the motion vector of every voxel in the image is computed by interpolating the motion vectors of the selected points. Once the motion vector of each voxel has been estimated, the segmentation of the next image in the sequence is just the propagation of the segmentation of the former image. That technique is repeated until every image in the sequence has been analyzed.

The definition of time and the order of a sequence can be reversed for the purpose of the analysis. For example, in a time series of cancer lesions in the liver, there may be more lesions in the final scan than were present in the initial scan. Thus, the 4D model can be run in the reverse direction to make sure all lesions are accounted for. Similarly, a long time series can be run from a mid-point, with analysis proceeding both forward and backward from the mid-point.

Finite-element models (FEM) are known for the analysis of images and for time-evolution analysis. The present invention follows a similar approach and recovers the point correspondence by minimizing the total energy of a mesh of masses and springs that models the physical properties of the anatomy. In the present invention, the mesh is not constrained by a single structure in the image, but instead is free to model the whole volumetric image, in which topological properties are supplied by the first segmented image and the physical properties are supplied by the a priori properties and the first segmented image. The motion estimation approach is an FEM-based point correspondence recovery algorithm between two consecutive images in the sequence. Each node in the mesh is an automatically selected feature point of the image sought to be tracked, and the spring stiffness is computed from the first segmented image and a priori knowledge of the human anatomy and typical biomechanical properties for muscle, bone and the like.

Many deformable models assume that a vector force field that drives spring-attached point masses can be extracted from the image. Most such models use that approach to build semi-automatic feature extraction algorithms. The present invention employs a similar approach and assumes that the image sampled at t=n is a set of three dynamic scalar fields:

$$\Phi(x,t)=\{g_n(x), |\nabla g_n(x)|, \nabla^2 g_n(x)\},$$

namely, the gray-scale image value, the magnitude of the gradient of the image value, and the Laplacian of the image value. Accordingly, a change in $\Phi(x, t)$ causes a quadratic change in the scalar field energy $U_\Phi(x) \propto (\Delta\Phi(x))^2$. Furthermore, the structures underlying the image are assumed to be modeled as a mesh of spring-attached point masses in a state of equilibrium with those scalar fields. Although equilibrium assumes that there is an external force field, the shape of the force field is not important. The distribution of the point masses is assumed to change in time, and the total energy change in a time period $\Delta t$ after time t=n is given by $$\Delta U_n(\Delta x) = \sum_{\forall X \in g_n} \left[ (\alpha(g_n(x) - g_{n+1}(x+\Delta x)))^2 + (\beta(|\nabla g_n(x)| - |\nabla g_{n+1}(x+\Delta x)|))^2 + (\gamma(\nabla^2 g_n(x) + \nabla^2 g_{n+1}(x+\Delta x)))^2 + \frac{1}{2}\eta \Delta X^T K \Delta X \right]$$

where $\alpha$, $\beta$, and $\gamma$ are weights for the contribution of every individual field change, $\eta$ weighs the gain in the strain energy, K is the FEM stiffness matrix, and $\Delta X$ is the FEM node displacement matrix. Analysis of that equation shows that any change in the image fields or in the mesh point distribution increases the system total energy. Therefore, the point correspondence from $g_n$ to $g_{n+1}$ is given by the mesh configuration whose total energy variation is a minimum. Accordingly, the point correspondence is given by $$\hat{X}=X+\Delta\hat{X}$$

where $$\Delta\hat{X}=\min_{\Delta X} \Delta U_n(\Delta X).$$

In that notation, $\min_p$ q is the value of p that minimizes q.

While the equations set forth above could conceivably be used to estimate the motion (point correspondence) of every voxel in the image, the number of voxels, which is typically over one million, and the complex nature of the equations make global minimization difficult. To simplify the problem, a coarse FEM mesh is constructed with selected points from the image at step 305. The energy minimization gives the point correspondence of the selected points.

The selection of such points is not trivial. First, for practical purposes, the number of points has to be very small, typically$\cong 10^4$; care must be taken that the selected points describe the whole image motion. Second, region boundaries are important features because boundary tracking is enough for accurate region motion description. Third, at region boundaries, the magnitude of the gradient is high, and the Laplacian is at a zero crossing point, making region boundaries easy features to track. Accordingly, segmented boundary points are selected in the construction of the FEM.

Although the boundary points represent a small subset of the image points, there are still too many boundary points for practical purposes. In order to reduce the number of points, constrained random sampling of the boundary points is used for the point extraction step. The constraint consists of avoiding the selection of a point too close to the points already selected. That constraint allows a more uniform selection of the points across the boundaries. Finally, to reduce the motion estimation error at points internal to each region, a few more points of the image are randomly selected using the same distance constraint. Experimental results show that between 5,000 and 10,000 points are enough to estimate and describe the motion of a typical volumetric image of 256×256×34 voxels. Of the selected points, 75% are arbitrarily chosen as boundary points, while the remaining 25% are interior points. Of course, other percentages can be used where appropriate.

Once a set of points to track is selected, the next step is to construct an FEM mesh for those points at step 307. The mesh constrains the kind of motion allowed by coding the material properties and the interaction properties for each region. The first step is to find, for every nodal point, the neighboring nodal point. Those skilled in the art will appreciate that the operation of finding the neighboring nodal point corresponds to building the Voronoi diagram of the mesh. Its dual, the Delaunay triangulation, represents the best possible tetrahedral finite element for a given nodal configuration. The Voronoi diagram is constructed by a dilation approach. Under that approach, each nodal point in the discrete volume is dilated. Such dilation achieves two purposes. First, it is tested when one dilated point contacts another, so that neighboring points can be identified. Second, every voxel can be associated with a point of the mesh.

Once every point $x_i$ has been associated with a neighboring point $x_j$, the two points are considered to be attached by a spring having spring constant $k_{i,j}^{l,m}$, where l and m identify the materials. The spring constant is defined by the material interaction properties of the connected points; those material interaction properties are predefined by the user in accordance with known properties of the materials. If the connected points belong to the same region, the spring constant reduces to $k_{i,j}^{l,l}$ and is derived from the elastic properties of the material in the region. If the connected points belong to different regions, the spring constant is derived from the average interaction force between the materials at the boundary. If the object being imaged is a human shoulder, the spring constant can be derived from a table such as the following:

|              | Humeral head | Muscle | Tendon | Cartilage |
|--------------|--------------|--------|--------|-----------|
| Humeral head | $10^4$       | 0.15   | 0.7    | 0.01      |
| Muscle       | 0.15         | 0.1    | 0.7    | 0.6       |
| Tendon       | 0.7          | 0.7    | 10     | 0.01      |
| Cartilage    | 0.01         | 0.6    | 0.01   | $10^2$    |

In theory, the interaction must be defined between any two adjacent regions. In practice, however, it is an acceptable approximation to define the interaction only between major anatomical components in the image and to leave the rest as arbitrary constants. In such an approximation, the error introduced is not significant compared with other errors introduced in the assumptions set forth above.

Spring constants can be assigned automatically, as the approximate size and image intensity for the bones are usually known a priori. Segmented image regions matching the a priori expectations are assigned to the relatively rigid elastic constants for bone. Soft tissues and growing or shrinking lesions are assigned relatively soft elastic constants.

Once the mesh has been set up, the next image in the sequence is input at step 309, and the energy between the two successive images in the sequence is minimized at step 311. The problem of minimizing the energy U can be split into two separate problems: minimizing the energy associated with rigid motion and minimizing that associated with deformable motion. While both energies use the same energy function, they rely on different strategies.

The rigid motion estimation relies on the fact that the contribution of rigid motion to the mesh deformation energy $(\Delta X^T K \Delta X)/2$ is very close to zero. The segmentation and the a priori knowledge of the anatomy indicate which points belong to a rigid body. If such points are selected for every individual rigid region, the rigid motion energy minimization is accomplished by finding, for each rigid region $R_i$, the rigid motion rotation $R_i$ and the translation $T_i$ that minimize that region's own energy:

$$\Delta X_{rigid} = \min_{\Delta x} U_{rigid} = \sum_{\forall l \in rigid} \left( \Delta \hat{X} = \min_{\Delta x_i} U_n(\Delta X_i) \right)$$

where $\Delta X_i = R_i X_i + T_i X_i$ and $\Delta \hat{x}_i$ is the optimum displacement matrix for the that belong to the rigid region $R_i$. That minimization problem has only six degrees of freedom for each rigid region: three in the rotation matrix and three in the translation matrix. Therefore, the twelve components (nine rotational and three translational) can be found via a six-dimensional steepest-descent technique if the difference between any two images in the sequence is small enough.

Once the rigid motion parameters have been found, the deformational motion is estimated through minimization of the total system energy U. That minimization cannot be simplified as much as the minimization of the rigid energy, and without further considerations, the number of degrees of freedom in a 3D deformable object is three times the number of node points in the entire mesh. The nature of the problem allows the use of a simple gradient descent technique for each node in the mesh. From the potential and kinetic energies, the Lagrangian (or kinetic potential, defined in physics as the kinetic energy minus the potential energy) of the system can be used to derive the Euler-Lagrange equations for every node of the system where the driving local force is just the gradient of the energy field. For every node in the mesh, the local energy is given by $$U_{x_i,n}(\Delta x) = (\alpha(g_n(x_i + \Delta x) - g_{n+1}(x_i)))^2 +$$
$$(\beta(|\nabla g_n(x_i + \Delta x)| - |\nabla g_{n+1}(x_i)|))^2 +$$
$$\gamma(\nabla^2 g_n(x_i + \Delta x) + \nabla^2 g_{n+1}(x_i))^2 +$$
$$\frac{1}{2}\eta \sum_{x_i \in G_m(x_i)} \left(k_{i,j}^{l,m}(x_j - x_i - \Delta x)\right)^2$$

where $G_m$ represents a neighborhood in the Voronoi diagram.

Thus, for every node, there is a problem in three degrees of freedom whose minimization is performed using a simple gradient descent technique that iteratively reduces the local node energy. The local node gradient descent equation is $$x_i(n+1) = x_i(n) - \nu \Delta U_{(x_i(n),n)}(\Delta x)$$

where the gradient of the mesh energy is analytically computable, the gradient of the field energy is numerically estimated from the image at two different resolutions, x(n+1) is the next node position, and v is a weighting factor for the gradient contribution.

At every step in the minimization, the process for each node takes into account the neighboring nodes' former displacement. The process is repeated until the total energy reaches a local minimum, which for small deformations is close to or equal to the global minimum. The displacement vector thus found represents the estimated motion at the node points.

Once the minimization process just described yields the sampled displacement field $\Delta X$, that displacement field is used to estimate the dense motion field needed to track the segmentation from one image in the sequence to the next (step 313). The dense motion is estimated by weighting the contribution of every neighbor mode in the mesh. A constant velocity model is assumed, and the estimated velocity of a voxel x at a time t is $v(x, t) = \Delta x(t)/\Delta t$. The dense motion field is estimated by $$v(x, t) = \frac{c(x)}{\Delta t} \sum_{\forall \Delta x_j \in G_m(x_i)} \frac{k^{l,m} \Delta x_j}{|x - x_j|}$$

where $$c(x) = \left[ \sum_{\forall \Delta x_j \in G_m(x_i)} \frac{k^{l,m}}{|x - x_j|} \right]^{-1}$$

$k^{l,m}$ is the spring constant or stiffness between the materials l and m associated with the voxels x and $x_j$, $\Delta t$ is the time interval between successive images in the sequence, $|x-x_j|$ is the simple Euclidean distance between the voxels, and the interpolation is performed using the neighbor nodes of the closest node to the voxel x. That interpolation weights the contribution of every neighbor node by its material property $$k_{i,j}^{l,m};$$

thus, the estimated voxel motion is similar for every homogeneous region, even at the boundary of that region.

Then, at step 315, the next image in the sequence is filled with the segmentation data. That means that the regions determined in one image are carried over into the next image. To do so, the velocity is estimated for every voxel in that next image. That is accomplished by a reverse mapping of the estimated motion, which is given by $$v(x, t+\Delta t) = \frac{1}{H} \sum_{\forall [x_j + v(x_j,t)] \in S(x)} v(x_j, t)$$

where H is the number of points that fall into the same voxel space S(x) in the next image. That mapping does not fill all the space at time t+Δt, but a simple interpolation between mapped neighbor voxels can be used to fill out that space. Once the velocity is estimated for every voxel in the next image, the segmentation of that image is simply $$L(x,t+\Delta t) = L(x-v(x,t+\Delta t)\Delta t, t)$$

where L(x,t) and L(x,t+Δt) are the segmentation labels at the voxel x for the times t and t+Δt.

At step 317, the segmentation thus developed is adjusted through relaxation labeling, such as that done at steps 211 and 215, and fine adjustments are made to the mesh nodes in the image. Then, the next image is input at step 309, unless it is determined at step 319 that the last image in the sequence has been segmented, in which case the operation ends at step 321.

First-order measurements—length, diameter and their extensions to area and volume—are quite useful quantities. However, they are limited in their ability to assess subtle but potentially important features of tissue structures or substructures. Thus, the inventors propose to use "higher order" measures of structure and shape to characterize biomarkers. The inventors define "higher order" measures as any measurements that cannot be extracted directly from the data using traditional manual or semi-automated techniques, and that go beyond simple pixel counting.

Figure 4:
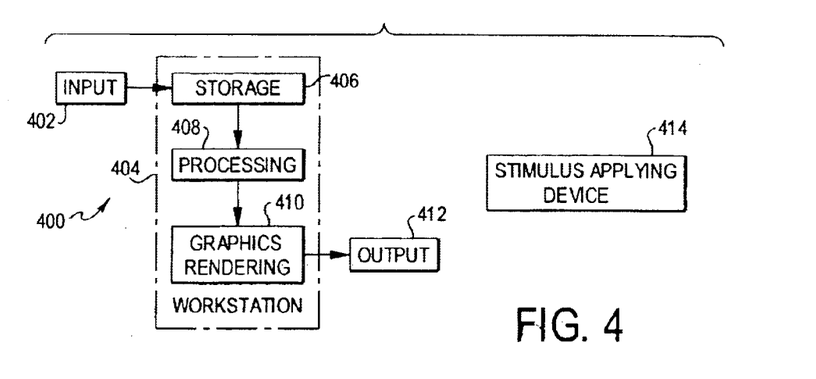
FIG. 4 shows a block diagram of a system on which the process of FIGS. 1–3 can be implemented.

The operations described above can be implemented in a system such as that shown in the block diagram of FIG. 4. System 400 includes an input device 402 for input of the image data, the database of material properties, and the like. The information input through the input device 402 is received in the workstation 404, which has a storage device 406 such as a hard drive, a processing unit 408 for performing the processing disclosed above to provide the 4D data, and a graphics rendering engine 410 for preparing the 4D data for viewing, e.g., by surface rendering. An output device 412 can include a monitor for viewing the images rendered by the rendering engine 410, a further storage device such as a video recorder for recording the images, or both. A device 414 for applying the stimulus can be provided; the device can be any suitable device, such as a source for applying radiotherapy, a mechanical device for applying pressure or another mechanical stimulus, or an injector for applying a chemical or biological agent. Illustrative examples of the workstation 404 and the graphics rendering engine 410 are a Silicon Graphics Indigo workstation and an Irix Explorer 3D graphics engine.

While a preferred embodiment of the present invention has been set forth in detail above, those skilled in the art who have reviewed the present disclosure will readily appreciate that other embodiments can be realized within the scope of the invention. For example, other biomarkers and stimuli can be used, as can other statistical techniques. Therefore, the present invention should be construed as limited only by the appended claims.

What is claimed is:

1. A method for assessing at least one biomarker in a region of interest of a patient and a response of the at least one biomarker to an applied stimulus, the method comprising:

(a) obtaining at least one pre-stimulus 3D image data set in the region of interest before the applied stimulus is applied to the at least one biomarker;

(b) applying the stimulus to the at least one biomarker, wherein the applied stimulus is an applied energy, an externally applied force, or a treatment modality;

(c) obtaining at least one post-stimulus 3D image data set in the region of interest after the applied stimulus is applied to the at least one biomarker; and (d) extracting biomarker measurements from the at least one pre-stimulus 3D image data set and the at least one post-stimulus 3D image data set.

2. The method of claim 1, wherein steps (a)–(c) result in a plurality of 3D image data sets, and wherein step (d) comprises identifying the at least one biomarker in one of the plurality of 3D image data sets through statistical reasoning.

3. The method of claim 2, wherein step (c) further comprises identifying the at least one biomarker in remaining ones of the plurality of 3D image data sets in accordance with an identification of the at least one biomarker identified in said one of the plurality of images through motion tracking and estimation.

4. The method of claim 3, wherein step (d) further comprises forming a 4D model of the region of interest.

5. The method of claim 3, wherein the plurality of 3D image sets are separated in time, and wherein said one of the plurality of 3D image sets is a first one in time of the plurality of 3D image sets.

6. The method of claim 3, wherein the plurality of 3D image sets are separated in time, and wherein said one of the plurality of 3D image sets is a last one in time of the plurality of 3D image sets.

7. The method of claim 3, wherein the plurality of 3D image sets are separated in time, and wherein said one of the plurality of 3D image sets is an intermediate one in time of the plurality of 3D image sets.

8. The method of claim 1, wherein the biomarker measurements comprise at least one higher-order measurement.

9. The method of claim 8, wherein the at least one higher-order measurement comprises a measurement selected from the group consisting of eigenfunction decompositions, moments of inertia, shape analysis, results of morphological operations, fractal analysis, wavelet analysis, advanced surface and shape analysis, and trajectories of bones, joints, tendons, and moving musculoskeletal structures.

10. The method of claim 1, wherein the at least one biomarker comprises a biomarker related to cancer.

11. The method of claim 10, wherein the biomarker related to cancer is selected from the group consisting of:

tumor surface area;

tumor compactness;

tumor surface curvature;

tumor surface roughness;

necrotic core volume;

necrotic core compactness;

necrotic core shape;

viable periphery volume;

volume of tumor vasculature;

change in tumor vasculature over time;

tumor shape;

morphological surface characteristics;

lesion characteristics;

tumor characteristics;
tumor peripheral characteristics;
tumor core characteristics;
bone metastases characteristics;
ascites characteristics;
pleural fluid characteristics;
vessel structure characteristics;
neovasculature characteristics;
polyp characteristics;
nodule characteristics;
angiogenisis characteristics;
tumor length;
tumor width; and
tumor 3D volume.

12. The method of claim 1, wherein the at least one biomarker comprises a biomarker related to joint disease.

13. The method of claim 12, wherein the biomarker related to joint disease is selected from the group consisting of:
shape of a subchondral bone plate;
layers of cartilage and their relative size;
signal intensity distribution within the cartilage layers;
contact area between articulating cartilage surfaces;
surface topology of cartilage shape;
intensity of bone marrow edema;
separation distances between bones;
meniscus shape;
meniscus surface area;
meniscus contact area with cartilage;
cartilage structural characteristics;
cartilage surface characteristics;
meniscus structural characteristics;
meniscus surface characteristics;
pannus structural characteristics;
joint fluid characteristics;
osteophyte characteristics;
bone characteristics;
lytic lesion characteristics;
prosthesis contact characteristics;
prosthesis wear;
joint spacing characteristics;
tibia medial cartilage volume;
tibia lateral cartilage volume;
femur cartilage volume;
patella cartilage volume;
tibia medial cartilage curvature;
tibia lateral cartilage curvature;
femur cartilage curvature;
patella cartilage curvature;
cartilage bending energy;
subchondral bone plate curvature;
subchondral bone plate bending energy;
meniscus volume;
osteophyte volume;
cartilage T2 lesion volumes;
bone marrow edema volume and number;
synovial fluid volume;
synovial thickening;
subchondral bone cyst volume and number;
kinematic tibial translation;
kinematic tibial rotation;
kinematic tibial valcus;
distance between vertebral bodies;
degree of subsidence of cage;
degree of lordosis by angle measurement;
degree of off-set between vertebral bodies;
femoral bone characteristics; and
patella characteristics.

14. The method of claim 1, wherein the at least one biomarker comprises a biomarker related to neurological disease.

15. The method of claim 14, wherein the biomarker related to neurological disease is selected from the group consisting of:
a shape, topology, and morphology of brain lesions;
shape, topology, and morphology of brain plaques;
shape, topology, and morphology of brain ischemia;
shape, topology, and morphology of brain tumors;
spatial frequency distribution of sulci and gyri;
compactness of gray matter and white matter;
whole brain characteristics;
gray matter characteristics;
white matter characteristics;
cerebral spinal fluid characteristics;
hippocampus characteristics;
brain sub-structure characteristics;
a ratio of cerebral spinal fluid volume to gray mater and white matter volume; and
a number and volume of brain lesions.

16. The method of claim 1, wherein the at least one biomarker comprises a biomarker related to disease and toxicity in an organ.

17. The method of claim 16, wherein the biomarker related to disease and toxicity is selected from the group consisting of:
organ volume;
organ surface;
organ compactness;
organ shape;
organ surface roughness; and
fat volume and shape.

18. A system for assessing at least one biomarker in a region of interest of a patent and a response of the at least one biomarker to an applied stimulus, the system comprising:
a stimulus applying device for applying the stimulus to the at least one biomarker, wherein the applied stimulus is an applied energy, an externally applied force, or a treatment modality;
an input device for receiving an input of (a) at least one pre-stimulus 3D image data set in the region of interest before the stimulus is applied to the at least one biomarker and (b) at least one post-stimulus 3D image data set in the region of interest after the stimulus is applied to the at least one biomarker; and
a computing device, in communication with the input device, for extracting biomarker measurements from the at least one pre-stimulus 3D image data set and the at least one post-stimulus 3D image data set.

19. The system of claim 18, wherein the input device receives a plurality of 3D image data sets, and wherein the computing device identifies the at least one biomarker in one of the plurality of 3D image data sets through statistical reasoning.

20. The system of claim 19, wherein the computing device identifies the at least one biomarker in remaining ones of the plurality of 3D image data sets in accordance with an identification of the at least one biomarker identified in said one of the plurality of images through motion tracking and estimation.

21. The system of claim 20, wherein the computing device forms a 4D model of the region of interest.

22. The system of claim 20, wherein the plurality of 3D image sets are separated in time, and wherein said one of the plurality of 3D image sets is a first one in time of the plurality of 3D image sets.

23. The system of claim 20, wherein the plurality of 3D image sets are separated in time, and wherein said one of the plurality of 3D image sets is a last one in time of the plurality of 3D image sets.

24. The system of claim 20, wherein the plurality of 3D image sets are separated in time, and wherein said one of the plurality of 3D image sets is an intermediate one in time of the plurality of 3D image sets.

25. The system of claim 18, wherein the biomarker measurements comprise at least one higher-order measurement.

26. The system of claim 25, wherein the at least one higher-order measurement comprises a measurement selected from the group consisting of eigenfunction decompositions, moments of inertia, shape analysis, results of morphological operations, fractal analysis, wavelet analysis, advanced surface and shape analysis, and trajectories of bones, joints, tendons, and moving musculoskeletal structures.

27. The system of claim 18, wherein the at least one biomarker comprises a biomarker related to cancer.

28. The system of claim 27, wherein the biomarker related to cancer is selected from the group consisting of:
tumor surface area;
tumor compactness;
tumor surface curvature;
tumor surface roughness;
necrotic core volume;
necrotic core compactness;
necrotic core shape;
viable periphery volume;
volume of tumor vasculature;
change in tumor vasculature over time;
tumor shape;
morphological surface characteristics;
lesion characteristics;
tumor characteristics;
tumor peripheral characteristics;
tumor core characteristics;
bone metastases characteristics;
ascites characteristics;
pleural fluid characteristics;
vessel structure characteristics;
neovasculature characteristics;
polyp characteristics;
nodule characteristics;
angiogenisis characteristics;
tumor length;
tumor width; and
tumor 3D volume.

29. The system of claim 18, wherein the at least one biomarker comprises a biomarker related to joint disease.

30. The system of claim 29, wherein the biomarker related to joint disease is selected from the group consisting of:
shape of a subchondral bone plate;
layers of cartilage and their relative size;
signal intensity distribution within the cartilage layers;
contact area between articulating cartilage surfaces;
surface topology of cartilage shape;
intensity of bone marrow edema;
separation distances between bones;
meniscus shape;
meniscus surface area;
meniscus contact area with cartilage;
cartilage structural characteristics;
cartilage surface characteristics;
meniscus structural characteristics;
meniscus surface characteristics;
pannus structural characteristics;
joint fluid characteristics;
osteophyte characteristics;
bone characteristics;
lytic lesion characteristics;
prosthesis contact characteristics;
prosthesis wear;
joint spacing characteristics;
tibia medial cartilage volume;
tibia lateral cartilage volume;
femur cartilage volume;
patella cartilage volume;
tibia medial cartilage curvature;
tibia lateral cartilage curvature;
femur cartilage curvature;
patella cartilage curvature;
cartilage bending energy;
subchondral bone plate curvature;
subchondral bone plate bending energy;
meniscus volume;
osteophyte volume;
cartilage T2 lesion volumes;
bone marrow edema volume and number;
synovial fluid volume;
synovial thickening;
subchondrial bone cyst volume and number;
kinematic tibial translation;
kinematic tibial rotation;
kinematic tibial valcus;
distance between vertebral bodies;
degree of subsidence of cage;
degree of lordosis by angle measurement;
degree of off-set between vertebral bodies;
femoral bone characteristics; and
patella characteristics.

31. The system of claim 18, wherein the at least one biomarker comprises a biomarker related to neurological disease.

32. The system of claim 31, wherein the biomarker related to neurological disease is selected from the group consisting of:
- a shape, topology, and morphology of brain lesions;
- shape, topology, and morphology of brain plaques;
- shape, topology, and morphology of brain ischemia;
- shape, topology, and morphology of brain tumors;
- spatial frequency distribution of sulci and gyri;
- compactness of gray matter and white matter;
- whole brain characteristics;
- gray matter characteristics;
- white matter characteristics;
- cerebral spinal fluid characteristics;
- hippocampus characteristics;
- brain sub-structure characteristics;
- a ratio of cerebral spinal fluid volume to gray mater and white matter volume; and
- a number and volume of brain lesions.

33. The system of claim 18, wherein the at least one biomarker comprises a biomarker related to disease and toxicity in an organ.

34. The system of claim 33, wherein the biomarker related to disease and toxicity is selected from the group consisting of:
- organ volume;
- organ surface;
- organ compactness;
- organ shape;
- organ surface roughness; and
- fat volume and shape.

* * * * *